United States Patent [19]

Christensen

[11] Patent Number: Plant 7,157

[45] Date of Patent: Feb. 20, 1990

[54] ROSE PLANT AROTRUSIM

[75] Inventor: Jack E. Christensen, Ontario, Calif.

[73] Assignee: Bear Creek Gardens, Inc., Somis, Calif.

[21] Appl. No.: 272,729

[22] Filed: Nov. 17, 1988

[51] Int. Cl.[4] ..... A01H 5/00

[52] U.S. Cl. ..... Plt./29

[58] Field of Search ..... Plt./28–29

*Primary Examiner*—Robert E. Bagwill

*Attorney, Agent, or Firm*—Majestic, Parsons, Siebert & Hsue

[57] ABSTRACT

A rose variety of the Floribunda class is provided that bears shapely crimson buds in clusters or two or three on a relatively long stem and has a vigorous, upright plant that needs little care and is better than average in resistance to disease and cold.

1 Drawing Sheet

SUMMARY OF THE INVENTION

The present invention relates to a new and distinct variety of rose plant of the Floribunda class, which was originated by me by crossing the variety Mactrum, U.S. Plant Pat. No. 4,297, with the variety Jacink, U.S. Plant Pat. No. 4,089.

The primary objective of this breeding was to produce a new rose variety of the Floribunda class capable of growing vigorously on its own root system, as a hedge plant or along a fence, with red flower color, and having good bud and stem qualities and good overall disease resistance and cold hardiness. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. A vigorous, upright, medium height plant that is easily propagated on its own root system;
2. Red flowers;
3. Relatively long stems bearing irregular clusters of two or three flowers;
4. Long, pointed and shapely buds.

Asexual reproduction of this new variety by cuttings, as performed at Somis, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "Arotrusim". Throughout this specification, color names beginning with a smaller letter signify ordinary dictionary significance for the color, while color names beginning with a capital letter designate values based upon the R.H.S. Colour Chart of The Royal Horticultural Society of London, England.

Observations of the buds and flowers were made from specimens grown in a greenhouse at Somis, Calif. in January.

Flower

The blooming habit is continuous. The bud size is one-half inch in height when the petals start to unfurl. The bud form is long and pointed. The bud color when sepals first divide is red between near Red Group 53A and near Red Group 53B. When half blown, both the upper and lower sides of the petals are red between near Red Group 53B and near Red Group 53C. The sepals are between near Green Group 143A and near Green Group 143B. The outer surface is smooth with scattered stipitate glands, while the inner surface is uniformly covered with a fine wooly tomentum. There are three lightly appendaged sepals, and two unappendaged sepals with a hairy edge. The receptacle color is near Green Group 143A. The receptacle has a funnel shape, a somewhat long size, and a smooth surface. The peduncle is of medium length and has a smooth surface with some stipitate glands. The peduncle is light green and erect. Opening is by petal unfurling, and is about average in duration.

Bloom

Bloom size is medium to large, with an average open size of between four and four and one-half inches. The blooms are borne singly and in irregular clusters of two to three flowers. The stems are of normal strength and are medium to long in length. The form when first open is high center and is retained to the end with a slight flattening. Under normal conditions there are 26 to 30 petals. The variety produces bright red flower petals surrounding golden anthers with red filaments and a light yellow stigma. The upper side and the reverse side of the petals at the flower center are both near Red Group 53A to Red Group 53B. There is a small white spot near White Group 155D near the base of the petals. The major color on the upper and lower sides is between near Red Group 54A and near Red Group 53B. There are no variegations. The general tonality at the end of the first day shows no change in color. At the end of the third day, the flowers fade to a more pinkish color near Red Group 53C or near Red Group 53D.

The fragrance is slight. The petals have a good texture and are round to obovate in shape with slightly recurved tips. The arrangement is imbricated with a few petaloids in the center. The blooms drop off cleanly, and last both on the plant and as a cut flower for a fair to long time.

Reproductive Parts

The anthers are yellow, of medium size, and are partly tucked in the calyx. The filaments are red, the pollen is gold yellow, and the stigmas are yellow. The styles are pink between near Red Group 49A and near Red Group 49B.

Plant

The plant has vigorous, upright growth of medium height in bush and shrub form.

Foliage

The foliage is large and abundant. The new foliage is reddish brown and the old foliage is matt green. A normal mid-stem leaf has seven leaflets.

The leaflets have an oval pointed shape with a leathery, non-glossy texture, and have a single serrated edge. Petiole rachis is green and has some prickles on the underside. Stipules are medium and serrated. The foliage has better than average disease resistance. It is resistant to mildew and has some resistance to blackspot under normal growing conditions at Somis, Calif.

Wood

New wood is reddish colored with a smooth bark. Old wood is green with a rough bark.

Prickles

There are an ordinary number of prickles on the main canes from the base and on the laterals from the main canes. The prickles are medium in size and are hooked downward. The prickles are red colored when young. There are a few small prickles on the main stalks and no small prickles on the laterals.

Parentage

The seed parent was of the variety Mactrum. The pollen parent was oh the variety Jacink.

Classification

Botanical is rosa hybrid. Commercial is Floribunda.

I claim:

1. A new and distinct variety of rose plant and parts thereof of the Floribunda class, characterized particularly as to novelty by the long shapely buds of crimson produced in clusters of usually two to three flowers on relatively long stems and the vigorous, upright plant which grows well on its own root system, requires little care, and has better than average disease resistance and above average cold hardiness, essentially as described and illustrated herein.

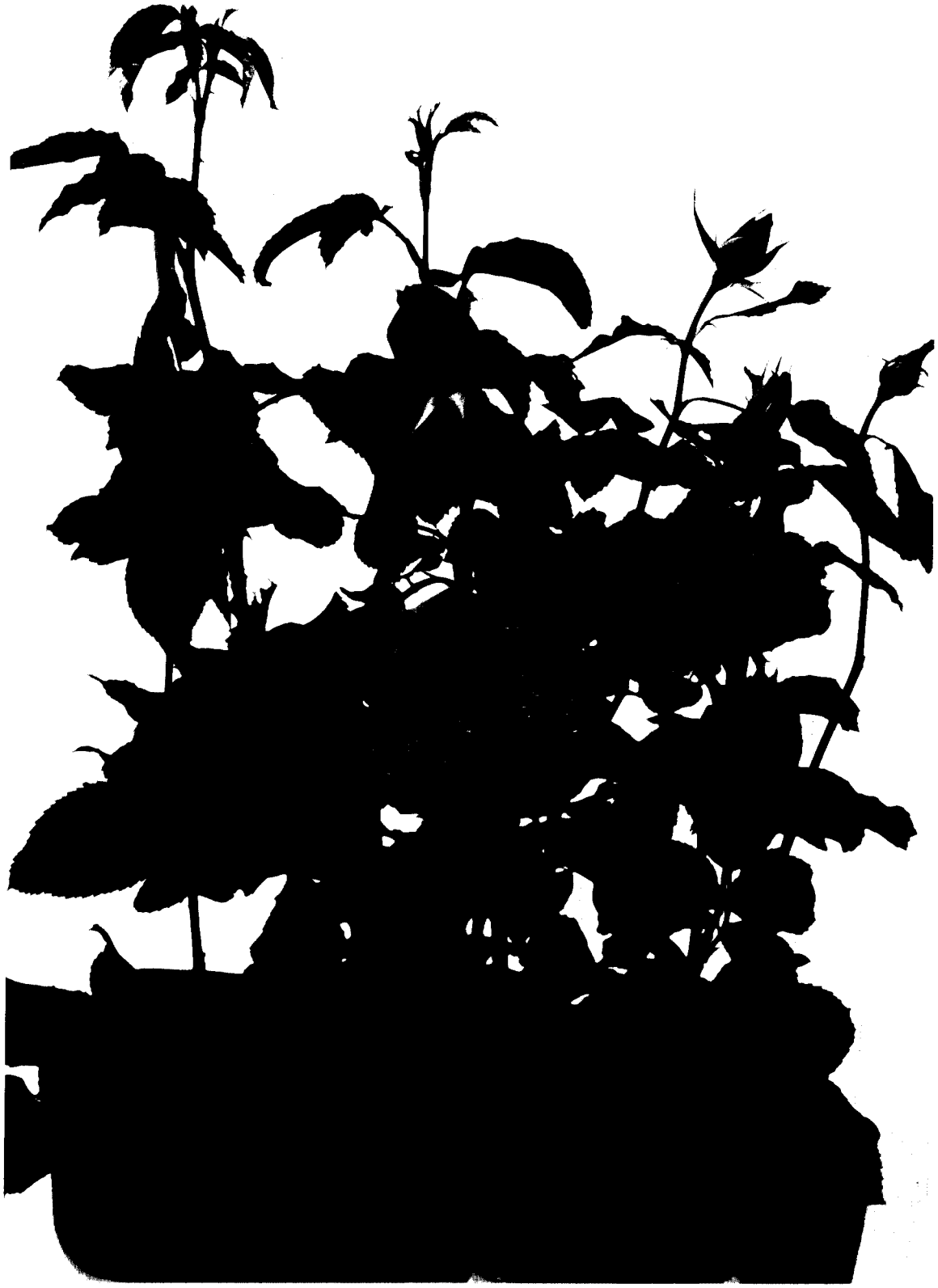

* * * * *